United States Patent
Mendes et al.

(10) Patent No.: US 6,245,109 B1
(45) Date of Patent: *Jun. 12, 2001

(54) ARTIFICIAL JOINT SYSTEM AND METHOD UTILIZING SAME FOR MONITORING WEAR AND DISPLACEMENT OF ARTIFICIAL JOINT MEMBERS

(75) Inventors: David Mendes; Ruth Beer, both of Haifa; Emanuel Mendes, Petach-Tikva, all of (IL)

(73) Assignee: IntelliJoint Systems, Ltd., Nes Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/585,318

(22) Filed: Jun. 2, 2000

Related U.S. Application Data

(63) Continuation of application No. 09/443,113, filed on Nov. 18, 1999.

(51) Int. Cl.$^7$ ........................................................ A61F 2/30
(52) U.S. Cl. ...................... 623/18.11; 623/18.12; 623/22.13
(58) Field of Search ............................. 623/18.11, 18.12, 623/22.24, 22.13, 23.16, 23.49, 16.11; 600/12

(56) References Cited

U.S. PATENT DOCUMENTS

| | | | | |
|---|---|---|---|---|
| 3,140,712 | * | 7/1964 | Hunter ........................... | 623/18.12 |
| 4,024,588 | * | 5/1977 | Janssen et al. ................ | 623/18.12 |
| 4,214,322 | * | 7/1980 | Kraus ............................ | 623/18.12 |
| 4,978,323 | * | 12/1990 | Freedman ...................... | 600/12 |
| 5,715,837 | * | 2/1998 | Chen ............................. | 600/12 |
| 5,935,171 | * | 8/1999 | Schneider et al. ............. | 623/22.13 |

* cited by examiner

*Primary Examiner*—Pedro Philogene

(57) ABSTRACT

An artificial joint system is provided herein. The system includes an artificial joint implantable within an individual, the artificial joint including artificial joint members each having an articulating surface and a bone attachment surface, wherein the articulating surfaces are in articulative engagement therebetween. The system further includes a detection system implanted within, or attached to, the artificial joint members and/or the bones to which the members are attached. The detection system serves for communicating an information signal receivable outside the body, the information signal indicative of a parameter associated with displacement between an artificial joint member and a bone to which it is attached and/or to wear or relative displacement of the articulating surfaces.

33 Claims, 6 Drawing Sheets

ARTIFICIAL JOINT SYSTEM AND METHOD UTILIZING SAME FOR MONITORING WEAR AND DISPLACEMENT OF ARTIFICIAL JOINT MEMBERS

This application is a continuation of Ser. No. 09/443,113 filed Nov. 18, 1999.

FIELD AND BACKGROUND OF THE INVENTION

The present invention relates to artificial joint system and to a method utilizing same capable of detecting the extent of relative displacement between an artificial joint member and a natural bone of the joint to which the artificial joint member is attached. More specifically, the present invention relates to an artificial joint system which includes a detection system capable of determining a distance between a joint member and reference points of the natural bone to which it is attached thereby enabling to determine the extent of relative displacement therebetween and the extent of deterioration of the natural bone of the joint. The present invention also relates to artificial joint system which includes a detection system for monitoring wear and displacement of articulating surfaces of the artificial joint members. Total joint artiroplasty is an operation involving the replacement of a damaged joint with an artificial joint assembly in order to restore motion to the joint and function to the muscles and ligaments and other soft tissue structures that operate and control the joint.

The operation is typically performed on individuals with a painful, disabling arthritic joint that is no longer responsive to conservative treatment regimens. This operation typically entails implantation of two or more artificial joint members into respective natural joint members so as to replace deteriorated natural articulating surfaces with artificial equivalents..

Artificial joint assemblies have been devised for a variety of joints including hips, knees, ankles, shoulders, elbows, and wrists (see, as examples, FIGS. 1a–k). Typically, components of artificial joints such as that shown in, for example, U.S. Pat. No. 4,068,342 to Townley et al. mimic the structure and function of joint members of a natural joint, thus providing as natural as possible articulation motion.

While artificial joint components are designed to provide stable and permanent attachment to the natural adjacent body tissue(s), at attachment interfaces, motion and/or loosening of the artificial joint member can occur, resulting in artificial joint relocation, which can lead to a loss of function, bone deterioration and tissue debris generation.

Such relocation can lead to an increase in wear to the articulating surfaces of the artificial joint. Such wear typically results in reduced function of the artificial joint and, in addition, produces joint debris which are expelled from the joint area to the surrounding tissues and may cause adverse reactions, such as inflammatory granulatoma, in these tissues.

The debris expelled from the artificial joint includes microscopic particles typically measuring up to a few microns in size. These particles provoke various tissue reactions, which affect the bones hosting the artificial joint implant.

The type and severity of the biological reaction to wear generated particles depend mainly on the physical properties and to a lesser degree also on the chemical properties of the wear particles. For example, in joints which include polyethylene component three types of particles are observed, chunks, flakes and granules. The granules, which are approximately one micron in size, are responsible for an intense inflammatory reaction. The histology is characterized by phagocytosis of the particles, resulting in large conglomerations of macrophages due to their inability to digest the polyethylene. The inflammatory process is accompanied by release of biochemical mediators such as prostaglandins and interleukins that cause absorption of the host native bone. Wear particles of other plastics, such as acetyl-copolymer, are of similar physical shapes but may cause an even more intense reaction.

Wear in metallic and ceramic joints is typically characterized by small granules which are taken in by macrophages, leading to a similar biochemical reaction to that caused by plastics.

As a wear of a joint progresses and larger amount of particles are expelled to the surrounding tissues, further bone absorption and loosening of the joint implant may occur. Such loosening of a prosthetic joint implant and damage to surrounding tissues is often left undetected in a patient even if regularly checked by a physician. Most modern methods currently employed for determining the extent of loosening and/or wear of an artificial joint, rely upon either X-ray, computer tomography, isotope bone scan or magnetic resonance to image the implanted joint and are of insufficient accuracy or technically difficult to perform and/or interpret even by highly skilled professionals. In fact, the most modern joint replacement assemblies incorporate metal backed plastic components, metallic components, or ceramic components within metallic shells and as such the available imaging methods cannot produce sufficient contrast in order to determine artificial joint loosening and/or articulating surface wear.

As a result of inefficient detection methods, oftentimes the only indication of early joint loosening is the pain and discomfort suffered by the patient. Oftentimes bone absorption progresses to a stage necessitating replacement surgery using larger implants, and/or bone grafts to accommodate for the lost bone tissue. The prognosis for success and service life of the implant after such a corrective operation is less predictable and depends, among other factors, on the extent of bone absorption suffered. If performed relatively early on, such corrective surgery has an increased chance of success. Therefore, a method to detect the extent and depth of wear of the articulating surfaces of an artificial joint is of paramount importance both to the patient and the treating physician.

There is thus a widely recognized need for, and it would be highly advantageous to have, an artificial joint system which enables to monitor relative displacement of artificial joint members and wear to the articulating surfaces thereof, thus enabling a treating physician to detect joint loosening in an individual prior to bone deterioration and absorption and significant damage to articulating surfaces.

SUMMARY OF THE INVENTION

According to one aspect of the present invention there is provided an artificial joint system comprising: (a) at least one artificial joint member having an articulating surface and a bone attachment portion, the bone attachment portion being for attaching the at least one artificial joint member to at least one natural bone of a joint when implanted within an individual; (b) a detection system implanted within, or attached to, the at least one artificial joint member and the at least one natural bone of the joint, the detection system being for communicating an information signal receivable outside the body, the information signal indicative of a parameter associated with relative displacement between the at least one artificial joint member and the at least one natural bone of the joint.

According to another aspect of the present invention there is provided a method of determining a parameter associated with relative displacement between an artificial joint member and a natural bone of a joint to which it is attached, the method comprising the steps of: (a) providing a detection system implanted within, or attached to, at least one location in at least one artificial joint member and at least one location in at least one natural bone of a joint, the detection system being for communicating an information signal receivable outside the body, the information signal indicative of a parameter associated with the distance and the relative displacement between the at least one artificial joint member and the at least one natural bone of the joint; (b) extracorporeally energizing the detection system so as to receive outside the body the information signal; and (c) processing the information signal being received so as to yield the parameter associated with the relative displacement between the at least one artificial joint member and the at least one natural bone of a joint.

According to another aspect of the present invention there is provided an artificial joint system comprising: (a) an artificial joint assembly implantable within an individual, the artificial joint assembly including a first artificial joint member having a first articulating surface and further including a second artificial joint member having a second articulating surface, the first and the second articulating surfaces being in articulative engagement therebetween; (b) a detection system implanted within, or attached to, the artificial joint assembly, the detection system being for communicating an information signal receivable outside the body, the information signal indicative of a parameter associated with wear or relative displacement of the articulating surfaces.

According to another aspect of the present invention there is provided a method of determining a parameter associated with wear or relative displacement of an artificial joint, the method comprising the steps of: (a) providing an artificial joint assembly system including: (i) an artificial joint assembly implantable within an individual, the artificial joint assembly including a first artificial joint member having a first articulating surface and further including a second artificial joint member having a second articulating surface, the first and the second articulating surfaces being in articulative engagement therebetween; and (ii) a detection system implanted within, or attached to, the artificial joint assembly, the detection system being for communicating an information signal receivable outside the body, the information signal indicative of a parameter associated with wear or relative displacement of the articulating surfaces; (b) extracorporeally energizing the detection system so as to receive outside the body the information signal indicative of a parameter associated with wear or relative displacement of the articulating surfaces; and (c) processing the information signal received so as to yield the parameter associated with the wear or relative displacement of the articulating surfaces.

According to further features in preferred embodiments of the invention described below, the artificial joint system further comprising an extracorporeal unit, the extracorporeal unit being for communicating to the detection system an energizing signal and further being for receiving from the detection system the information signal indicative of a parameter associated with wear or relative displacement of the articulating surfaces.

According to still further features in the described preferred embodiments the detection system includes at least one resonance circuit element implanted within or attached to the first artificial joint member and at least one magnetic (e.g., ferromagnetic, paramagnetic, ferrimagnetic or metamagnetic) element implanted within, attached to, or forming a part of the second artificial joint member, such that when the at least one resonance circuit element is energized the at least one resonance circuit produces a signal of oscillating frequency which is a function of a distance between the at least one resonance circuit element and the at least one magnetic (e.g., ferromagnetic, paramagnetic, ferrimagnetic or metamagnetic) element, the distance being the parameter associated with the wear or relative displacement of the articulating surfaces.

According to still further features in the described preferred embodiments the at least one resonance circuit element includes plurality of distinct resonance circuit elements implanted within or attached to the first artificial joint member, each of the plurality of distinct resonance circuit elements producing a distinct signal of oscillating frequency upon being energized, the distinct signal being a function of a distance between a resonance circuit element of the plurality of distinct resonance circuit elements and the at least one magnetic (e.g., ferromagnetic, paramagnetic, ferrimagnetic or metamagnetic) element.

According to still further features in the described preferred embodiments the artificial joint assembly is selected from the group consisting of an artificial shoulder joint, an artificial hip joint, an artificial knee joint, an artificial elbow joint, an artificial ankle joint, an artificial wrist joint, an artificial carpo-metacarpal joint, an artificial metacarpo-phalangeal joints, an artificial interphalangeal joint and an artificial metatarso-phalangeal joint.

According to still further features in the described preferred embodiments the artificial joint assembly further includes a third artificial joint member having at least one additional articulating surface, the at least one additional articulating surface being in articulative engagement with at least one of the first and the second articulative surfaces.

According to still further features in the described preferred embodiments the detection system includes at least one resonance circuit element implanted within or attached to the first artificial joint member, and at least two magnetic (e.g., ferromagnetic, paramagnetic, ferrimagnetic or metamagnetic) elements implanted within, or attached to, the second and the third artificial joint members, such that when the at least one resonance circuit element is energized it produces a signal of oscillating frequency which is a function of a distance between the resonance circuit element and each of the magnetic elements, the distance being the parameter associated with the wear or relative displacement of the articulating surfaces.

According to still further features in the described preferred embodiments the first and the second artificial joint members are each fabricated from at least one material selected from the group consisting of stainless steel, titanium alloy, cobalt alloy, polymeric material, ceramics and composites materials.

According to still further features in the described preferred embodiments the first and the second and the third artificial joint members each include a stem portion distant to the articulating surface thereof, the portion being for attaching each of the first and the second artificial joint members to a bone when implanted within the individual.

The present invention successfully addresses the shortcomings of the presently known configurations by providing a system with which a wear and displacement of members of an implanted artificial joint assembly can be determined at various time points during the service life of the artificial joint assembly in an easy and accurate manner.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1A:
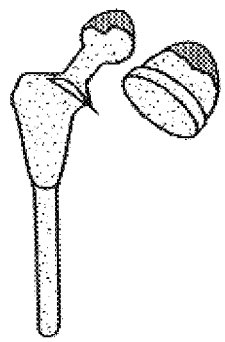
FIGS. 1a–k are prior art designs of various artificial joint assemblies including artificial hip joint components (FIGS. 1a–d), artificial knee joint components (FIGS. 1e–g), artificial ankle joint component (FIG. 1h), artificial shoulder joint components (FIG. 1i), artificial elbow joint components (FIG. 1j), and artificial wrist joint components (FIG. 1k).
Figure 1B:
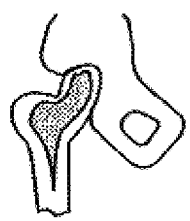
Figure 1C:
Figure 1D:
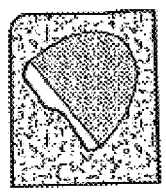
Figure 1E:
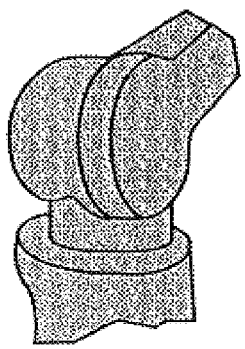
Figure 1F:
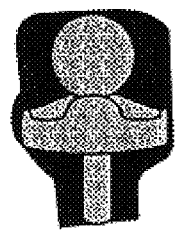
Figure 1G:
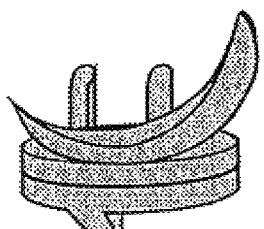
Figure 1H:
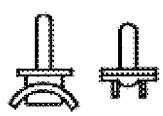
Figure 1I:
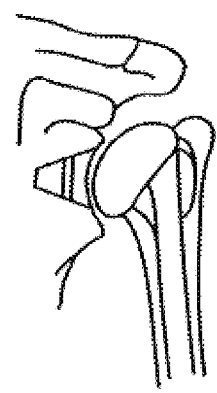
Figure 1J:
Figure 1K:
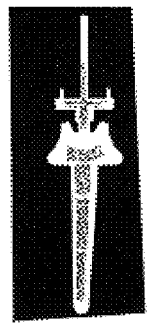

The present invention is of a system and method which can be utilized for monitoring and detecting displacement and wear in artificial joint members. Specifically, the present invention is of an artificial joint system which includes implanted or attached detection system(s) which can be used to detect the wear and displacement of artificial joint members by communicating outside the body a signal which includes information indicative of a distance between a member of the artificial joint and reference points in a bone to which it is attached and/or a distance between the articulating surfaces of artificial joint members.

The principles and operation of the system and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
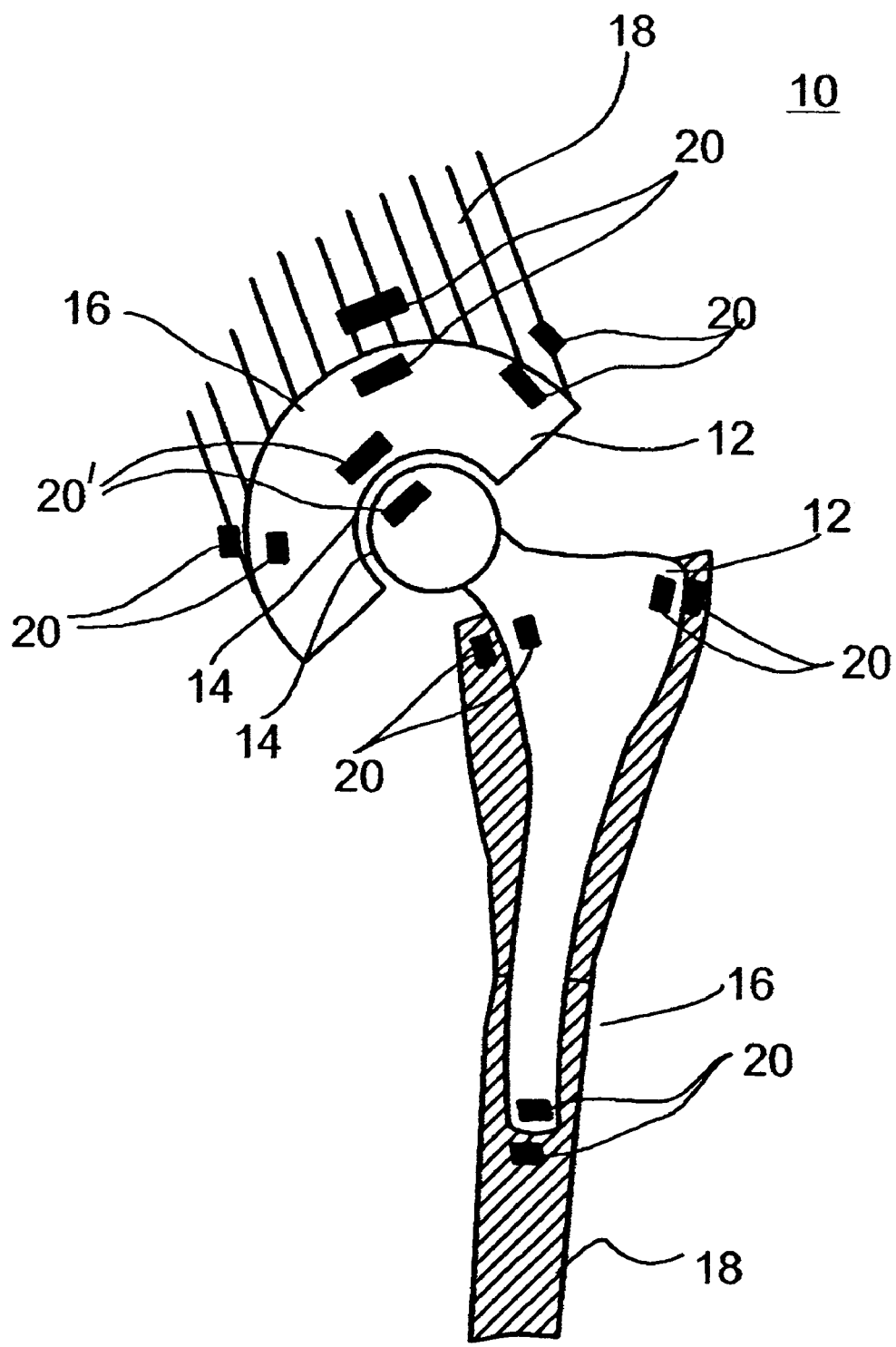
FIG. 2 is a cross sectional view of an artificial hip joint according to the present invention including a first detection system for monitoring displacement between the artificial joint member and the natural bone of the joint to which it is attached and a second detection system for monitoring relative displacement between the articulating surfaces of the two artificial joint members.

Referring to the drawings, FIG. 2 illustrates an artificial joint system according to the teachings of the present invention, which is referred to herein as system 10.

According to one aspect of the present invention, system 10 includes at least one artificial joint member 12 (two are shown). Member(s) 12 can be for example, artificial hip joint member(s) (as exemplified in FIG. 2), artificial knee joint member(s), artificial ankle joint member(s), artificial shoulder joint member(s), artificial elbow joint member(s), or artificial wrist joint member(s).

Each of members 12 has an articulating surface 14 and a bone attachment portion 16. Bone attachment portion 16 serves for attaching member 12 to a natural bone of a joint 18, when members 12 are implanted within a joint of an individual. Bone attachment portion 16 can include protrusions and/or other projections or indentations which facilitate attachment of members 12 to bones 18. Fixation of members 12 to bones 18 can be effected, for example, by polymethylmethacrylate cementing. Alternatively, fixation can be effected by creating a porous surface on a metal or polymer from which members 12 are fabricated, which porous surface allows for bone ingrowth following implantation, which results in fixation. Creating a porous surface can be effected by plasma spray of metallic granules or fibers or by coating a core metal or plastic with a porous layer of active calcium phosphate ceramics, such as hydroxyapatite or tricalcium phosphate. Alternatively, a porous layer of titanium powder or a titanium net can be applied to the core.

Members 12 are each fabricated from at least one material such as, but not limited to, stainless steel, titanium alloy, cobalt alloy, polymeric material such as, but not limited to, polyethylene, ceramics and/or composite materials.

System 10 further includes a detection system 20 implanted within, or attached to members 12 and bones 18 of the joint. Detection system 20 serves for communicating an information signal receivable outside the body. This information signal is indicative of a parameter associated with relative displacement between member(s) 12 and bone(s) 18.

Detection system 20 employs any number of unique element pairs of known electronic properties which are attached to, or implanted within members 12 and bones 18 in at least one location (three shown in FIG. 2). These elements enable to measure a distance between members 12 and reference points in bones 18 via the mutual electronic properties of the elements. To be able to measure a distance, the mutual area of the two element planes and the capacitance between the two planes represented by the dielectric constant of the space between the planes must be known. Thus, assuming that the space between the planes of the elements is partially filled with air the capacitance measured between the elements planes is function of the distance therebetween.

One method to produce a signal indicative of a capacitance is to connect a capacitor to a coil forming a resonant circuit and to measure the resonant frequency of the circuit as transmitted from the coil. By providing a magnetic (e.g., ferromagnetic, paramagnetic, ferrimagnetic or metamagnetic) element in varying distances from the resonant circuit a distance dependent capacitance as reflected by the resonance of the coil is produced. This method is advantageous in that the resonant frequency can be remotely measured, thus, allowing contact-less measurement, by remotely energizing the circuit and measuring the frequency of the free oscillations of the resonant circuit.

It will be appreciated that detection system 20 can be utilized for two-dimensional and/or three-dimensional assessment of joint member displacement. For example, by implanting detection system 20 at three or more locations in bone 18 and member 12 (as is shown in FIG. 2), one can obtain information on the relative displacement between bone 18 and member 12 in three different planes. This can be achieved, for example, by comparing three dimensional data acquired from detection systems 20 immediately following joint replacement surgery with data acquired following use of the joint for a period of time. Such a comparison, which can be performed by commercially available software programs capable of analyzing and displaying three dimensional data, can yield information on relative displacement in three different planes, thus providing a more accurate assessment of the state of the implanted joint members at any given time.

Detection system 20 is similar in construction and operation to detection system 20' which is described in detail hereinbelow with respect to further embodiments of the present invention.

Thus, system 10 of the present invention enables to monitor and detect relative displacement between member 12 and bone 18. Such monitoring is advantageous since detection of displacement between a joint bone and an implanted or attached artificial joint member can be indicative, for example, of joint loosening and/or bone deterioration which often necessitates treatment or replacement.

It will be appreciated, that since wear to articulating surfaces 14 of members 12 is also a problem frequently experienced in implanted artificial joints, members 12 can alternatively or additionally include an additional detection system which is similar to detection system 20, and which functions in monitoring and detecting relative displacement between articulating surfaces 14 of members 12.

Figure 3:
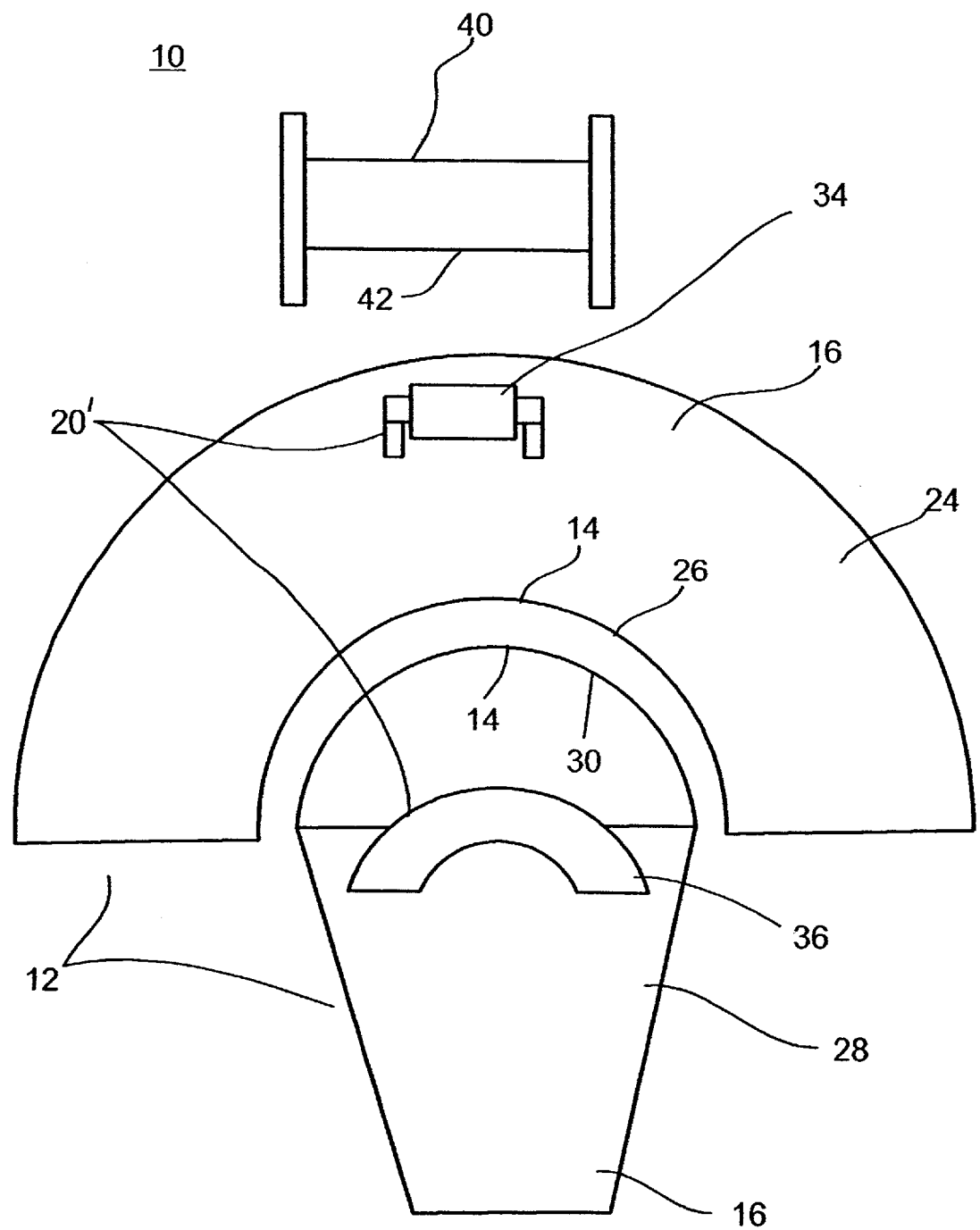
FIG. 3 is a schematic depiction of an artificial joint system showing an extracorporeal unit, and an implantable artificial joint assembly including one embodiment of a detection system according to the present invention.
Figure 4:
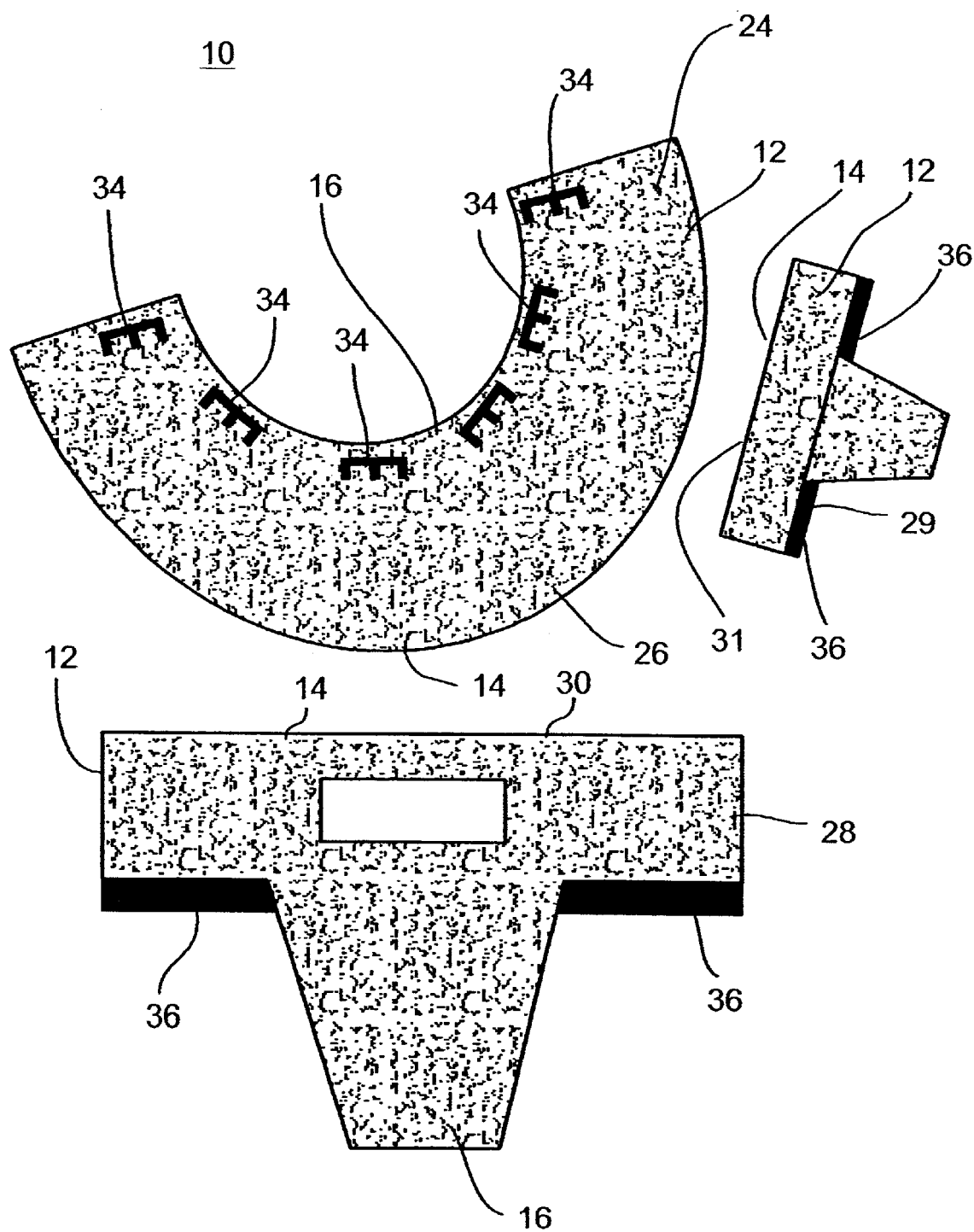
FIG. 4 is a schematic depiction of a three joint member embodiment of an implantable artificial joint assembly according to the present invention.

Thus, as shown in FIGS. 2, 3 and 4, and according to another aspect of the present invention, members 12 include detection system 20'.

Members 12 include a first artificial joint member 24 having a first articulating surface 26. Artificial joint members 12 further includes a second artificial joint member 28 having a second articulating surface 30. Articulating surfaces 26 and 30 are in articulative engagement therebetween, so as to allow movement of members 12 relative to one another. This movement is restricted by design to mimic those of a natural joint which is replaced by the artificial joint.

As is specifically shown in FIG. 4, artificial joint members 12 can further include a third artificial joint member 29, such as the case of, for example, an artificial knee joint assembly. Member 29 includes a third articulating surface 31. In this case, members 12 are configured such that surface 31 is in articulative engagement with at least one of surfaces 26 and 30.

Members 12, or the articulating surfaces thereof are fabricated so as to have distinct properties in friction, lubrication and wear. Friction depends on the coefficient property of the material, the diameter of the component from the center of motion and the finish property of the surface. Lubrication is the property of the synovial fluid which is known to be deficient after surgical arthroplasty. Wear is the property of the two articulating surfaces and depends, among other factors, on sphericity, surface finish and lubrication.

Stainless steel or cobalt alloy used in combination with polyethylene is present state of the art. However following 10 years of service, a joint manufactured from these materials may produce about 1 mm of linear wear, which results in a release of billions or more of particles into the surrounding tissues. Coupling titanium alloy with polyethylene results in a large amount of wear of both the plastic and the titanium due to currently inapt polishing technologies.

Coupling ceramic with polyethylene results in about 50% decrease of wear in comparison to metal and polyethylene, which is a significant improvement, but still causes release of billions of particles over a ten year period. Coupling metal to metal and ceramic to ceramic has been tried to a limited extent, yet with uncertain results.

Detection system 20' according to this aspect of the present invention, is implanted within, or attached to, members 12.

Preferably, detection system 20' is implanted within members 12 during the fabrication thereof. Detection system 20' serves for communicating an information signal receivable outside the body, which information signal is indicative of a parameter associated with wear or relative displacement of the articulating surfaces.

It will be appreciated that either wear of surfaces 26 and 30 and/or relative displacement of members 12 can lead to a change in a distance between defined points or regions within members 12. Therefore, measurement of the distance between defined points within members 12 at any given time can yield information on both the wear of surfaces 26 and 30 and/or relative displacement of members 12. It will further be appreciated that in cases of more than two members 12, detection system 20' is configured such that a distance is measurable between, for example, any pair of members 12.

Detection system 20' can also be utilized to measure specific distances between three or more defined point-pairs in members 12. Such measurements can provide information on a volumetric wear of surfaces 26 and 30 which can serve, based on material characteristics of surfaces 26 and 30, to assess the volume and number of particle debris expelled from the artificial joint over a period of time.

It will further be appreciated that in the case of an artificial joint which includes both detection system 20 and detection system 20', each detection system is configured such that a distance between the articulating surfaces and a distance between each member 12 and the reference point of the bone to which it is attached can be separately measured.

The following is a detailed description of various embodiments of detection system 20'. It will be appreciated however, that these embodiments also apply to detection system 20 mentioned above.

According to one preferred embodiment of the present invention, and as specifically shown in FIG. 3, detection system 20' includes at least one resonance circuit element 34 implanted within or attached to member 24. Preferably, resonance circuit element 34 includes a coil with a ferromagnetic core which can be, for example, U or E shaped.

Resonance circuit element 34 can include for example, a cobalt-iron core preferably in an amorphous configuration, and a gold or cobalt wire coil. Detection system 20' further includes at least one magnetic (e.g., ferromagnetic, paramagnetic, ferrimagnetic or metamagnetic) element 36 implanted within, attached to, or forming a part of member 28. It will be appreciated that in cases where member 28 or a portion thereof is constructed of a magnetizable metal, such a portion can be utilized as magnetic element 36. As is specifically shown in FIG. 4, in the case of more than two members 12, additional elements 36 can be provided, such that the distance between any pair of members can be determined.

Element 36 is shaped so as to allows a magnetic loop with resonance circuit element 34. When resonance circuit element 34 is energized by an energy source originating from outside the body, it produces a signal of a distinct oscillating frequency which frequency is function of a distance between resonance circuit element 34 and element 36. Thus, movement of resonance circuit element 34 and element 36 relative to each other, as is caused by displacement of one of members 12, or alternatively by friction induced wear to surfaces 26 and/or 30, yields a resonance frequency different than that of a normally positioned, wear free members 12.

Thus, elements 34 and 36 form a high Q resonant circuit. The frequency of oscillation of a resonant circuit is a function of a distance between element 34 and element 36 which can be indicative of either wear of surfaces 26 and 30 or relative displacement of members 24 and 28.

Figure 5:
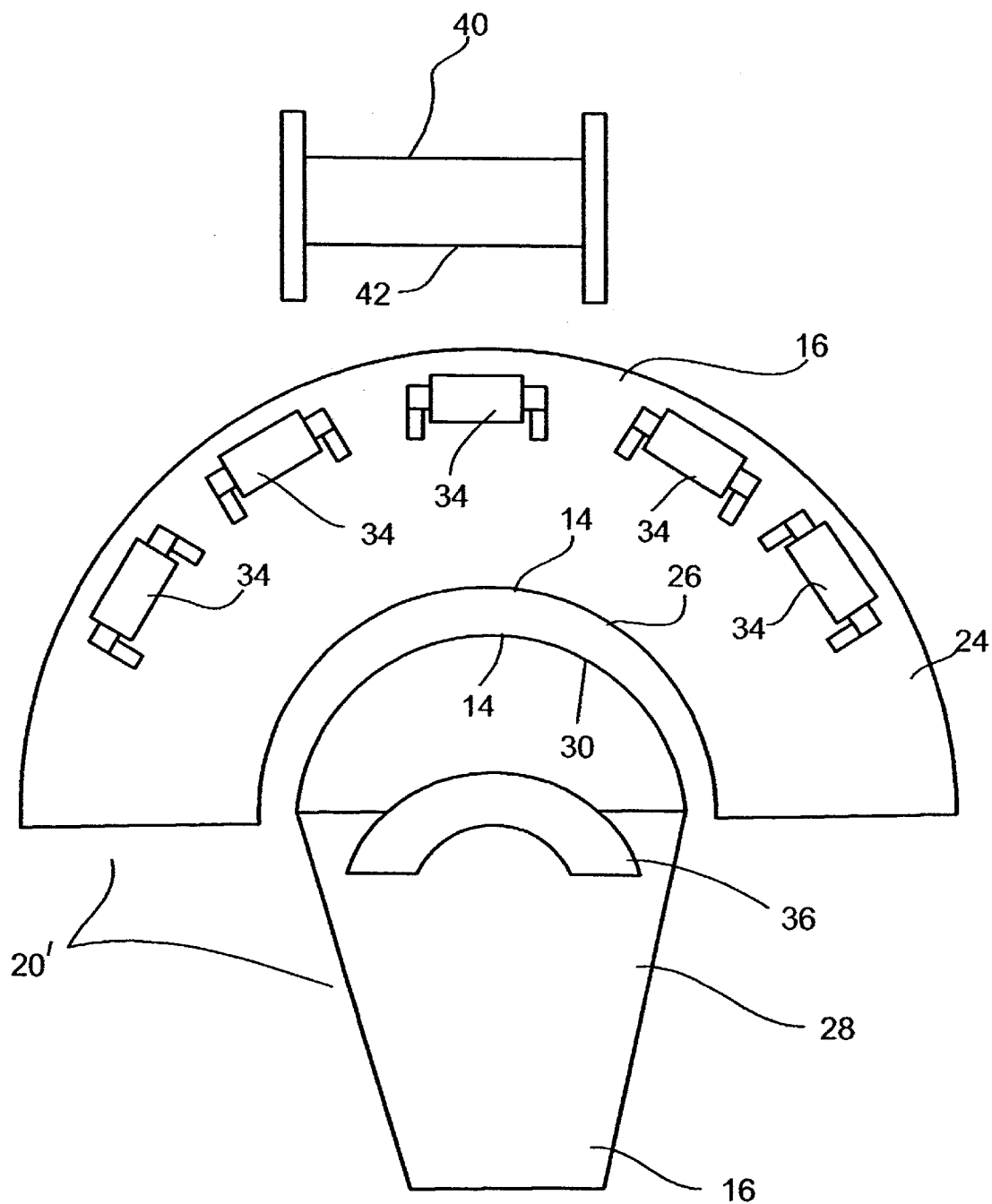
FIG. 5 is a schematic depiction of an artificial joint system showing an extracorporeal unit, and an implantable artificial joint assembly including another embodiment of a detection system according to the present invention.

It will be appreciated that in order to measure a distance change caused by relative displacement of members 24 and 28 which relative displacement can be asymmetric, several elements 34 are utilized in member 24 (as is specifically shown in FIG. 5). In this case, each element 34 is assigned a different resonant frequency, enabling to distinct distance measurement generated by the resonance frequency of each element. In order to measure volumetric wear of surfaces 26 and/or 30, as mentioned hereinabove, three or more pairs of elements 34 and 36, each having a unique resonant frequency, can be utilized to measure a distance between members 24 and 28 at three or more different regions thus yielding volumetric wear information.

Thus, according to the present invention, system 10 includes detection system 20 and/or 20' for monitoring displacement between member 12 and bone 18 and/or wear and displacement of articulating surfaces 14.

To provide the energy for energizing detection systems 20 and/or 20', system 10 further includes an extracorporeal unit 40. Extracorporeal unit 40 serves for communicating to element 34 of detection system 20 for example, an energizing signal and for receiving from element 34 a signal which is indicative of a distance between elements 34 and 36.

As shown in FIGS. 3 and 5, unit 40 includes a coil 42 which serves to both produce the energizing signal and to receive the signal generated by element 34. Alternatively unit 40 includes two coils one to produce a signal and one to receive a signal.

Thus, using unit 40 and implanted detection systems 20 and/or 20', a distance between member(s) 12 and bone(s) 18 which can be indicative of implant loosening or bone deterioration and/or a distance between elements 34 and 36 which can be indicative of wear to surfaces 26 and/or 30 and to relative displacement between members 24 and 28 can be measured.

Figure 6:
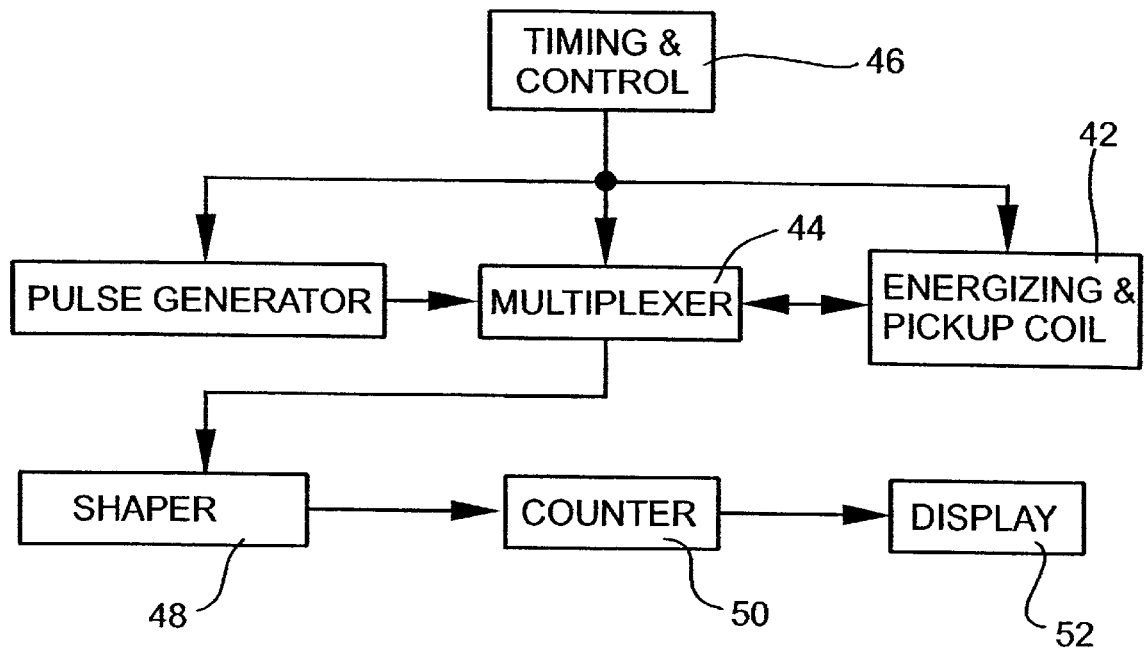
FIG. 6 is a black box diagram depicting the various components of one embodiment of an extracorporeal unit according to the present invention.

As is shown in FIGS. 5 and 6, such a measurement can be effected as follows. A short energizing pulse generated from coil 42 which, depending on the number of implanted elements, can be multiplexed by a multiplexer 44 and controlled by a timing control 46 is picked up by for example, element 34 of detection system 20'. Element 34 resonates at a frequency dependent on a distance from element 36. This resonance produces a transmitted signal oscillating at a distinct frequency, this frequency is picked-up by coil 42 of unit 40, which now functions as a pick-up coil. The picked up signal wave is shaped to a square wave by shaper 48, measured by a counter 50 and displayed to a user via display 52 as a distance value.

Figure 7:
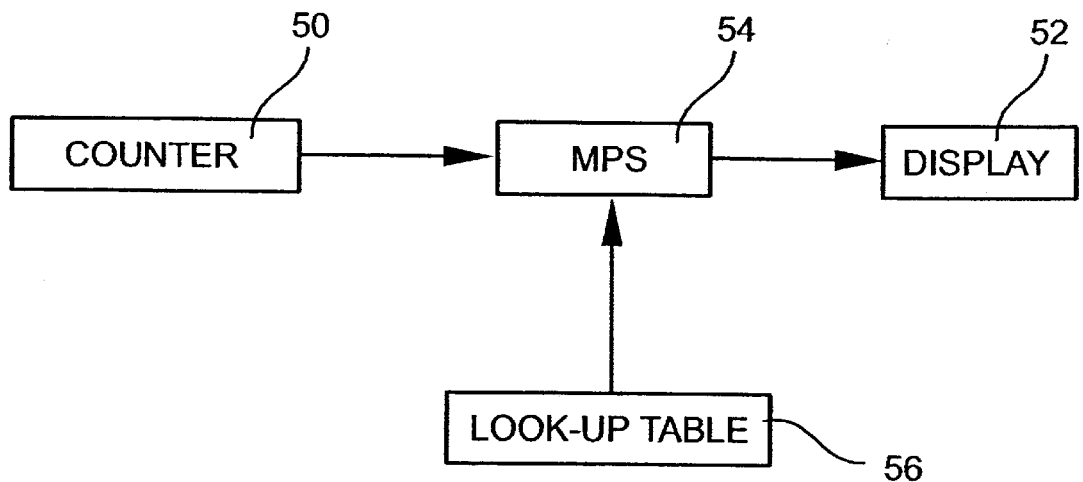
FIG. 7 is a black box diagram depicting some of the components of another embodiment of the extracorporeal unit according to the present invention.

Alternatively and as specifically shown in FIG. 7, the signal provided by counter 50 is fed into a microprocessor 54 which compares the signal to a lookup table 56. Lookup tables can be used in order to compensate for non-linearity in the distance to frequency ratio.

An example of a lookup table which can be utilized by the present invention to compensate for the non-linearity in the distance to frequency ratio is given hereinbelow, wherein f is the frequency and d is the distance as a function of the frequency measured.

| Frequency | 1 | 2 | 3 . . . d | (distance in mm) |
|---|---|---|---|---|
| f1 | f11 | f12 | f13 f1d | |
| f2 | f21 | f22 | f23 f2d | |
| f3 | f31 | f32 | f33 f3d | |
| ⋮ | | | | |
| fx | fx1 | fx2 | fx3 fxd | |

It will be appreciated that system 10 of the present invention enables the detection of extremely small changes in a distance between artificial joint member(s) and reference points in bone(s) and/or between the articulating surfaces of artificial joint members, which changes can be caused by, for example, artificial joint loosening, bone deterioration, and/or wear to the articulating surfaces of the artificial joint members.

For example, the resonance circuit configuration of detection systems 20 is capable of detecting a distance differential between two measured distances which is indicative of minimal displacement between bone 18 and member 12, while detection system 20' is capable of detecting a distance differential between two measured distances which is indicative of minimal wear to articulating surfaces of members 12.

To effect measurements in a most accurate manner an implanted artificial joint is first monitored when an individual regains motion capacity in the joint following recovery from implant surgery. The implanted artificial joint is then monitored for signs of wear and/or displacement at various time points following the initial measurement. Each oscillating frequency is either used directly to calculate a distance or alternatively inputted into a lookup table to determine a distance.

Such measurements yield both the state and function of the implanted artificial joint since an abnormally high rate of wear or displacement may be indicative of a poor fit or an unsuccessful implantation operation.

Thus, the system of the present invention enables accurate and simple monitoring of a state of an artificial joint implanted in an individual. The information providable by the system of the present invention enables a treating physician to detect early on, bone deterioration and implant loosening and/or any articulating surface wear which may lead to the development of bone absorption and/or loosening of the joint implant. Early detection of displacement and/or wear enables the physician to determine a most suitable course of treatment if necessary. In addition the system of the present invention allows a physician to detect displacements of joint members which can be at times left unnoticed by the patient or treating physician but which may progress into severe joint damage.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety.

What is claimed is:

1. An artificial joint system comprising:
   (a) at least one artificial joint member having an articulating surface and a bone attachment portion, said bone attachment portion being for attaching said at least one artificial joint member to at least one natural bone of a joint when implanted within an individual; and
   (b) a detection system implanted within, or attached to, said at least one artificial joint member and said at least one natural bone of said joint, said at least one detection system being for communicating an information signal receivable outside the body, said information signal indicative of a parameter associated with relative displacement between said at least one artificial joint member and said at least one natural bone of said joint.

2. The artificial joint system of claim 1, wherein said at least one artificial joint member includes at least two artificial joint members, each attached to a specific natural bone of said joint of said at least one natural bone of said joint, whereas said articulating surfaces of said at least two artificial joint members are configured to allow articulative engagement therebetween.

3. The artificial joint system of claim 1, further comprising an extracorporeal unit, said extracorporeal unit being for communicating to said detection system an energizing signal and further being for receiving from said detection system said information signal indicative of a parameter associated with relative displacement between said at least one artificial joint member and said at least one natural bone of said joint.

4. The artificial joint system of claim 1, wherein said detection system includes at least one resonance circuit element implanted within or attached to said at least one artificial joint member and at least one magnetic element implanted within, or attached to, said at least one natural bone of said joint and vice versa, such that when said at least one resonance circuit element is energized said at least one resonance circuit produces a signal of oscillating frequency which is a function of a distance between said at least one resonance circuit element and said at least one magnetic element, said distance being said parameter associated with relative displacement between said at least one artificial joint member and said at least one natural bone of said joint.

5. The artificial joint system of claim 4, wherein said at least one resonance circuit element includes a plurality of distinct resonance circuit elements each producing a distinct signal of oscillating frequency upon being energized, said distinct signal being a function of a distance between a specific resonance circuit element of said plurality of distinct resonance circuit elements and said at least one magnetic element.

6. The artificial joint system of claim 1, wherein said at least one artificial joint member forms a part of an artificial joint selected from the group consisting of an artificial shoulder joint, an artificial hip joint, an artificial knee joint, an artificial elbow joint, an artificial ankle joint, an artificial wrist joint, an artificial carpo-metacarpal joint, an artificial metacarpo-phalangeal joint, an artificial interphalangeal joint and an artificial metatarso-phalangeal joint.

7. The artificial joint system of claim 1, wherein said at least one artificial joint member is fabricated from at least one material selected from the group consisting of stainless steel, titanium alloy, cobalt alloy, polymeric material, ceramics and composites materials.

8. The artificial joint system of claim 4, wherein said at least one resonance circuit element is implanted within, or attached to, said bone attachment portion of said at least one artificial joint member, and further wherein said at least one magnetic element is implanted within, attached to, or forms a part of said bone attachment portion of said at least one artificial joint member.

9. The artificial joint system of claim 2, further comprising an additional detection system implanted within or attached to said at least two artificial joint members, said additional detection system serves for communicating an information signal receivable outside the body, said information signal indicative of a parameter associated with wear or relative displacement of said articulating surfaces of said at least two artificial joint members.

10. A method of determining a parameter associated with relative displacement between an artificial joint member and a natural bone of a joint to which it is attached, the method comprising the steps of:
   (a) providing a detection system implanted within, or attached to, least one artificial joint member and at least one natural bone of a joint, said detection system being for communicating an information signal receivable outside the body, said information signal indicative of a parameter associated with the relative displacement between said at least one artificial joint member and said at least one natural bone of said joint;
   (b) extracorporeally energizing said detection system so as to receive outside the body said information signal; and
   (c) processing said information signal being received so as to yield said parameter associated with the relative displacement between said at least one artificial joint member and said at least one natural bone of a joint.

11. The method of claim 10, wherein step (b) is effected by an extracorporeal unit, said extracorporeal unit being for communicating to said detection system an energizing signal and further being for receiving from said detection system said information signal indicative of said parameter associated with the relative displacement between said at least one artificial joint member and said at least one natural bone of said joint.

12. The method of claim 10, wherein said detection system includes at least one resonance circuit element implanted within or attached to said at least one artificial joint member and at least one magnetic element implanted within, or attached to, said at least one natural bone of said joint or vice versa, such that when said at least one resonance circuit element is energized said at least one resonance circuit produces a signal of oscillating frequency which is a function of a distance between said at least one resonance circuit element and said at least one magnetic element, said distance being said parameter associated with said wear or relative displacement of said articulating surfaces.

13. The method of claim 12, wherein said at least one resonance circuit element includes plurality of distinct resonance circuit elements each producing a distinct signal of oscillating frequency upon being energized, said distinct signal being proportional to a distance between a resonance circuit element of said plurality of distinct resonance circuit elements and said at least one magnetic element.

14. The method of claim 10, wherein said at least one artificial joint member is a part of an artificial joint selected from the group consisting of an artificial shoulder joint, an artificial hip joint, an artificial knee joint, an artificial elbow joint, an artificial ankle joint, an artificial wrist joint, an artificial carpo-metacarpal joint, an artificial metacarpo-phalangeal joint, an artificial interphalangeal joint and an artificial metatarso-phalangeal joint.

15. The method of claim 10, wherein said at least one artificial joint member is fabricated from at least one material selected from the group consisting of stainless steel, titanium alloy, cobalt alloy, polymeric material, ceramics and composite materials.

16. An artificial joint system comprising:
(a) an artificial joint assembly implantable within an individual, said artificial joint assembly including a first artificial joint assembly member having a first articulating surface and further including a second artificial joint assembly member having a second articulating surface, said first and said second articulating surfaces being in articulative engagement therebetween;
(b) a detection system implanted within, or attached to, said artificial joint assembly, said detection system being designed and configured for communicating an information signal receivable outside the body, said information signal indicative of a parameter associated with wear or relative displacement of said articulating surfaces.

17. The artificial joint system of claim 16, further comprising an extracorporeal unit, said extracorporeal unit being for communicating to said detection system an energizing signal and further being for receiving from said detection system said information signal indicative of a parameter associated with wear or relative displacement of said articulating surfaces.

18. The artificial joint system of claim 16, wherein said detection system includes at least one resonance circuit element implanted within or attached to said first artificial joint assembly member and at least one magnetic element implanted within, attached to, or forming a part of said second artificial joint assembly member, such that when said at least one resonance circuit element is energized said at least one resonance circuit produces a signal of oscillating frequency which is function of a distance between said at least one resonance circuit element and said at least one magnetic element, said distance being said parameter associated with said wear or relative displacement of said articulating surfaces.

19. The artificial joint system of claim 18, wherein said at least one resonance circuit element includes plurality of distinct resonance circuit elements implanted within or attached to said first artificial joint assembly member, each of said plurality of distinct resonance circuit elements producing a distinct signal of oscillating frequency upon being energized, said distinct signal being proportional to a distance between a resonance circuit element of said plurality of distinct resonance circuit elements and said at least one magnetic element.

20. The artificial joint system of claim 16, wherein said artificial joint assembly is an artificial shoulder joint, an artificial hip joint, an artificial elbow joint, an artificial ankle joint, an artificial wrist joint, an artificial carpo-metacarpal joint, an artificial metacarpo-phalangeal joint, an artificial interphalangeal joint and an artificial metatarso-phalangeal joint.

21. The artificial joint system of claim 16, wherein said artificial joint assembly further includes a third artificial joint assembly member having a third articulating surface, said third articulating surface being in articulative engagement with at least one of said first and said second articulative surfaces.

22. The artificial joint system of claim 16, wherein said artificial joint assembly is an artificial knee joint.

23. The artificial joint system of claim 16, wherein said first and said second artificial joint assembly members are each fabricated from at least one material selected from the group consisting of stainless steel, titanium alloy, cobalt alloy, polymeric material, ceramics and composite materials.

24. The artificial joint system of claim 16, wherein said first and said second artificial joint assembly members each include a portion distant to said articulating surface thereof, said portion being for attaching each of said first and said second artificial joint assembly members to a natural bone of a joint when implanted within the individual.

25. A method of determining a parameter associated with wear or relative displacement of an artificial joint, the method comprising the steps of:
(a) providing an artificial joint assembly system including:
    (i) an artificial joint assembly implantable within an individual, said artificial joint assembly including a first artificial joint assembly member having a first articulating surface and further including a second artificial joint assembly member having a second articulating surface, said first and said second articulating surfaces being in articulative engagement therebetween; and
    (ii) a detection system implanted within, or attached to, said artificial joint assembly, said detection system being for communicating an information signal receivable outside the body, said information signal indicative of a parameter associated with wear or relative displacement of said articulating surfaces; and
(b) extracorporeally energizing said detection system so as to receive outside the body said information signal indicative of a parameter associated with wear or relative displacement of said articulating surfaces; and
(c) processing said information signal received so as to yield said parameter associated with said wear or relative displacement of said articulating surfaces.

26. The method of claim 25, wherein step (b) is effected by an extracorporeal unit, said extracorporeal unit being for communicating to said detection system an energizing signal and fiber being for receiving from said detection system said information signal indicative of a parameter associated with wear or relative displacement of said articulating surfaces.

27. The method of claim 25, wherein said detection system includes at least one resonance circuit element implanted within or attached to said first artificial joint assembly member and at least one magnetic element implanted within, or attached to, said second artificial joint assembly member, such that when said at least one resonance circuit element is energized said at least one resonance circuit produces a signal of oscillating frequency which is function of a distance between said at least one resonance circuit element and said at least one magnetic element, said distance being said parameter associated with said wear or relative displacement of said articulating surfaces.

28. The method of claim 27, wherein said at least one resonance circuit element includes plurality of distinct resonance circuit elements implanted within or attached to said first artificial joint assembly member, each of said plurality of distinct resonance circuit elements producing a distinct signal of oscillating frequency upon being energized, said distinct signal being function of a distance between a resonance circuit element of said plurality of distinct resonance circuit elements and said at least one magnetic element.

29. The method of claim 25, wherein said artificial joint assembly is an artificial shoulder joint, an artificial hip joint an artificial elbow joint, an artificial ankle joint, an artificial wrist joint, an artificial carpo-metacarpal joint, an artificial metacarpo-phalangeal, an artificial interphalangeal joint and an artificial metatarso-phalangeal joint.

30. The method of claim 25, wherein said artificial joint assembly further includes a third artificial joint assembly member having a third articulating surface, said third articulating surface being in articulative engagement with at least one of said first and said second articulative surfaces.

31. The method of claim 25, wherein said artificial joint assembly is an artificial knee joint.

32. The method of claim 25, wherein said first and said second artificial joint assembly members are each fabricated from at least one material selected from the group consisting of stainless steels, titanium alloy, cobalt alloy, polymeric material, ceramics and composite materials.

33. The method of claim 25, wherein said first and said second artificial joint assembly members each include a portion distant to said articulating surface thereof, said portion being for attaching each of said first and said second artificial joint assembly members to a natural bone of a joint when implanted within the individual.

* * * * *